United States Patent [19]

Photis

[11] 4,443,623

[45] Apr. 17, 1984

[54] PREPARATION OF PREDOMINATELY METHYL ACRYLAMIDOGLYCOLATE METHYL ETHER IN A NORMALLY LIQUID PRODUCT

[75] Inventor: James M. Photis, Ridgefield, Conn.

[73] Assignee: American Cyanamid Company, Stamford, Conn.

[21] Appl. No.: 377,505

[22] Filed: May 12, 1982

[51] Int. Cl.$^3$ ............................................ C07C 102/00
[52] U.S. Cl. ..................................... 560/170; 560/186
[58] Field of Search ................................ 560/170, 186

[56] References Cited

U.S. PATENT DOCUMENTS

| 3,422,139 | 1/1969 | Talet | 562/567 |
| 4,156,093 | 5/1979 | Christidis | 560/126 |

FOREIGN PATENT DOCUMENTS

| 20000 | 12/1980 | European Pat. Off. | 560/170 |
| 1004158 | 3/1957 | Fed. Rep. of Germany | 560/186 |

Primary Examiner—Michael L. Shippen
Attorney, Agent, or Firm—Steven J. Hultquist

[57] ABSTRACT

Reaction of glyoxylic acid with a $C_3$ to $C_6$ alcohol capable of forming an azeotrope with water to form the $C_3$ to $C_6$ alkyl glyoxylate or alkyl glyoxylate alkyl hemiacetal, reacting the intermediate with acrylamide and optionally with a $C_3$ to $C_6$ alcohol to form the $C_3$ to $C_6$ alkyl acrylamidoglycolate or alkyl acrylamidoglycolate alkyl ether in essentially polymer free form which are readily converted by transesterification/etherification or transesterification/transetherification with methanol into predominately methyl acrylamidoglycolate methyl ether preferably in liquid form.

8 Claims, No Drawings

PREPARATION OF PREDOMINATELY METHYL ACRYLAMIDOGLYCOLATE METHYL ETHER IN A NORMALLY LIQUID PRODUCT

This invention relates to a process for preparing methyl acrylamidoglycolate methyl ether substantially free of polymeric byproducts and to a non-viscous liquid product comprising a major portion of methyl acrylamidoglycolate methyl ether. More particularly, this invention relates to such a process wherein $C_3$ to $C_6$ alkyl glyoxylate $C_3$ to $C_6$ alkyl ether hemiacetal is prepared by reaction of glyoxylic acid with a $C_3$ to $C_6$ alcohol, this intermediate is reacted with acrylamide and optionally with a $C_3$ to $C_6$ alcohol and the resulting product is converted to the desired product by transesterification/etherification or transesterification/transetherification with methanol.

Alkyl acrylamidoglycolate alkyl ethers have the general structure (1)

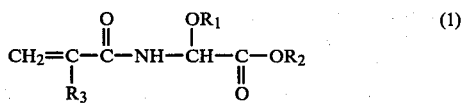

wherein $R_1$ and $R_2$ are the same or different and are selected from aliphatic or cycloaliphatic radicals of 1 to 6 carbon atoms and a hydroxyaliphatic or hydroxycycloaliphatic radical containing 2-6 carbon atoms in which the hydroxyl group is on the carbon atom adjacent that joined to the oxygen atom of the alkyl glyoxylate hemiacetal and $R_3$ is selected from H and $CH_3$. These compounds are highly desirable as crosslinking agents in coating applications. The preferred compounds are those in which both $R_1$ and $R_2$ are methyl radicals.

Methyl acrylamidoglycolate methyl ether has two major deficiencies associated with it in spite of its preference as a crosslinking agent. The pure product is a solid material having limited solubility in several common acrylate or methacrylate monomers. This complicates formulation of reaction mixtures and generally requires heating to completely dissolve the solid with the result that premature polymerization oftimes occurs in temperatue sensitive formulations.

A second deficiency associated with methyl acrylamidoglycolate methyl ether relates to the problems associated with its preparation. Conventional organic chemical methodology suggests that this compound can be prepared by the reaction of acrylamidoglycolic acid (2) with methyl alcohol in the presence of a suitable acid catalyst in accordance with Equation I.

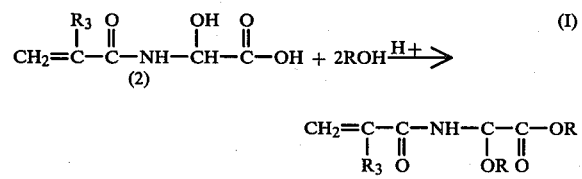

wherein $R_3$ is H or $CH_3$ and R is the radical remaining after removal of the OH group from the alcohol used. The process as shown in Equation I has been found to be inadequate for the preparation of alkyl acrylamidoglycolate alkyl ethers, particularly the desired methyl acrylamidoglycolate methyl ether. Even under conditions of azeotropic removal of byproduct water, which are possible when using an alcohol such as butanol, severe polymerization problems are encountered even with inhibitor present. In the presence of water and an acid catalyst compound (2) and/or intermediate product (3)

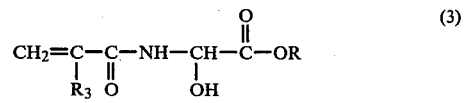

wherein the R's are as defined in Equation I, polymerize or revert back to acrylamide, and the acrylamide thus produced can polymerize. Polymerization of the product and/or intermediates and/or acrylamide by the combination of water and acid catalyst is further aggravated by the fact that compound (2) is obtained as a hydrate with water since it is produced from the reaction of aqueous glyoxylic acid and acrylamide. As a result it is necessary to remove three moles of water in order to obtain a compound of structure (1) from an appropriate compound of structure (2).

In accordance with the present invention, there is provided a process for preparing methyl acrylamidoglycolate methyl ether which comprises reacting glyoxylic acid with a $C_3$ to $C_6$ alcohol under conditions which lead to azeotropic removal of water to provide $C_3$ to $C_6$ alkyl glyoxylate alkyl hemiacetal, reacting said $C_3$ to $C_6$ alkyl glyoxylate alkyl hemiacetal with an acrylamide while removing volatiles therefrom to provide $C_3$ to $C_6$ alkyl acrylamidoglycolate and optionally reacting $C_3$ to $C_6$ alkyl acrylamidoglycolate with a $C_3$ to $C_6$ alcohol at elevated temperature in the presence of an acid catalyst while removing water and volatiles therefrom to provide $C_3$ to $C_6$ alkyl acrylamidoglycolate alkyl ether. Reaction of $C_3$ to $C_6$ alkyl acrylamidoglycolate alkyl ether with an excess of methanol in the presence of a transesterification/transetherification catalyst provides methyl acrylamidoglycolate methyl ether in major proportion. The ratio of methyl to $C_3$ to $C_6$ alkyl groups in the final product can be controlled by varying the initial ratio of methanol to $C_3$ to $C_6$ alkyl acrylamidoglycolate alkyl ether. The methyl acrylamidoglycolate methyl ether obtained in this manner is normally in a non-viscous, liquid form comprising a major portion of methyl acrylamidoglycolate methyl ether and a sufficient quantity of at least one of $C_3$ to $C_6$ alkyl acrylamidoglycolate $C_3$ to $C_6$ alkyl ether, $C_3$ to $C_6$ alkyl acrylamidoglycolate methyl ether, and methyl acrylamidoglycolate $C_3$ to $C_6$ alkyl ether to provide a non-viscous, liquid product.

The same non-viscuous, liquid mixture can be obtained by reacting excess methanol directly with the $C_3$ to $C_6$ alkyl acrylamidoglycolate in the presence of an a transesterification/etherification catalyst under essentially anhydrous conditions. In this case, the water formed by the etherification reaction is removed by codistillation with methanol as it is formed. Some of the $C_3$ to $C_6$ alcohol is also removed with the methanol.

Surprisingly, the process of the present invention provides the desired product under conditions which do not lead to polymerization and provides the product in non-viscuous, liquid form. If it is desired to obtain methyl acrylamidoglycolate methyl ether in solid or semi-solid form, such product can be readily obtained by repeating the last step of the process of the invention using fresh methanol and acid catalyst.

The improved technology provided by the present invention involves the reaction of glyoxylic acid with a $C_3$ to $C_6$ alcohol under conditions of azeotropic removal of water to give $C_3$ to $C_6$ alkyl glyoxylate alkyl hemiacetal (4) as shown in Equation II. The reactions are exemplified using the preferred alcohol, butanol.

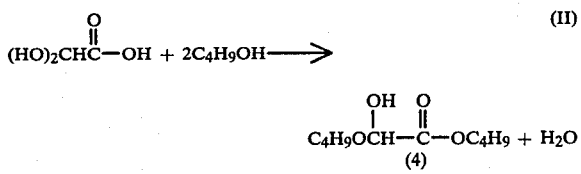

The intermediate (4) is then reacted with an acrylamide to give butyl acrylamidoglycolate (5) according to Equation III.

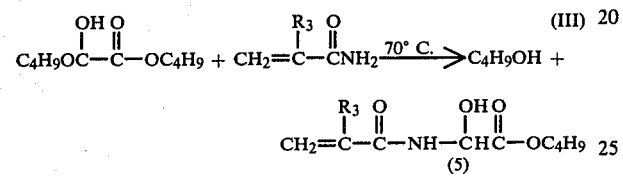

wherein $R_3$ is as defined above. Compound (5) reacted with butanol gives butyl acrylamidoglycolate butyl ether (6) free from polymeric contaminants according to Equation IV, $R_3$ being hydrogen.

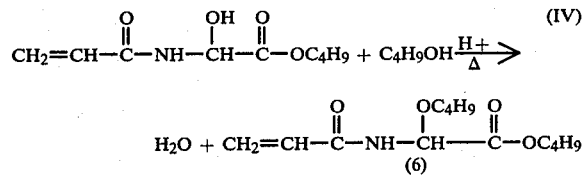

As indicated above, the most desirable alkyl acrylamidoglycolate alkyl ethers are those in which in structure (I) both $R_1$ and $R_2$ are methyl. Unfortunately, use of methyl alcohol in the reactions of Equations I, or II is not successful due to the fact that water is infinitely miscible with methanol and therefore cannot be efficiently separated from the reaction medium. Much polymerization occurs. Use of methanol in Equation II leads to incomplete reaction, i.e., the product is contaminated with glyoxylic acid methyl hemiacetal (7) according to Equation V.

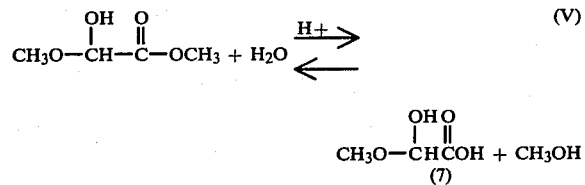

In carrying out the process of the present invention, as indicated glyoxylic acid is reacted with butanol under conditions which result in the removal of water as an azeotrope with excess butanol. Consequently, excess butanol is employed and any excess is removed after complete removal of water. Since the reaction involves azeotropic distillation, suitable temperatures and pressures must be employed.

After the desired butyl glyoxylate butyl hemiacetal is obtained as described above, it is reacted with acrylamide at elevated temperature to provide butyl acrylamidoglycolate with the release of one mole of butanol per mole of reactants. The alcohol is normally removed under rection conditions to provide a more complete addition.

After the desired butyl acrylamidoglycolate is obtained it may be reacted with butanol in the presence of an acid catalyst under conditions which lead to the azeotropic removal of water to provide butyl acrylamidoglycolate butyl ether. Again an excess of butanol is employed and removed when water removal is complete. A suitable acid catalyst is sulfuric acid and others known in the art for etherification reactions may be used. Additional inert solvents may be used to provide more efficient water removal or a more dilute reaction medium, if desired. The step described immediately above is an optional step and the process of the invention may be conducted without this step by reacting butyl acrylamidoglycolate with methanol in the subsequent step next described.

Using either butyl acrylamidoglycolate or butyl acrylamidoglycolate butyl ether, reaction is next conducted with methanol in the presence of an acid catalyst of the type describe above at elevated temperature while removing water and/or volatiles therefrom to provide methyl acrylamidoglycolate methyl ether in major proportion. Water will arise when butyl acrylamidoglycolate is employed as starting material in this reaction step but in the case where butyl acrylamidoglycolate butyl ether is employed as starting material in this reaction step butanol and excess methanol will form the principal volatiles.

Following reaction, the reaction mixture is preferably stripped of volatiles and the sulfuric acid catalyst is neutralized with magnesium oxide or other similar weak alkali such as calcium oxide, barium hydroxide octahydrate, sodium acetate or lithium hydroxide. Following catalyst neutralization, further stripping of volatiles if preferred, typically at 55° C. under vacuum with an air bleeder.

When the reaction is conducted in the manner described, the product is obtained in a non-viscous, liquid which is readily dissolved in acrylic monomers. The product consists of a major portion of methyl acrylamidoglycolate methyl ether and a minor amount of at least one of butyl acrylamidoglycolate butyl ether, methyl acrylamidoglycolate butyl ether and butyl acrylamidoglycolate methyl ether although as prepared all minor constituents are present. The particular proportions of minor constituents may vary widely while still providing a highly reactive non-viscous liquid product. It is only necessary for purposes of the product aspect of the present invention that the proportions of minor constituents, singly or in combination, provide the desired non-viscous liquid product. Generally, the non-viscous liquid product will contain at least about 5 weight percent of at least one of the minor constituents and, correspondingly, 95 weight percent or less of the major constituent which, by definition, must exceed 50 weight percent of the composition. Preferably the overall methyl/$C_3$-$C_6$ alkyl ratio of the final mixture will be 2.3 to b 19, and most preferably 9 to 19. An alternative procedure for obtaining the non-viscous, liquid product is to add the minor constituents in proper proportions to a solid methyl acrylamidoglycolate methyl ether and melt the mixture.

The invention is more fully illustrated by the examples which follow wherein all parts and percentages are by weight unless otherwise specified.

EXAMPLE 1

A suitable reaction vessel is charged with 524 parts (2.57 moles) of butyl glyoxylate butyl hemiacetal, 176 parts of acrylamide and 0.52 parts of monomethyl ether of hydroquinone. The mixture is heated with stirring at 70° C. for 2 hours. A solution of 3 ml of concentrated sulfuric acid in 250 ml each of butanol and butyl acetate is added. The reaction mixture is heated and stirred at 70°–74° C. and vacuum is then applied to reduce the pressure to 110–120 mm. Refluxing under a Dean-Stark trap with an air bleeder is maintained for one hour. Twenty-four milliliters of water are removed. Volatiles are then removed under reduced pressure. A solution of 3 ml sulfuric acid in 75 ml of methanol is added. Refluxing with the introduction of air below the surface of the reaction solution is maintained for 1.5–2 hours. The pot temperature is observed to rise from 72° to 75° C. Some volatiles are stripped under reduced pressure to lower the temperature to about 20° C. Ten parts of MgO are added. Volatiles are completely removed at 55° C. under vacuum with an air bleeder. The pale orange product is filtered through a pad of celite on a Buchner funnel. Yield is about 600 parts of a non-volatile, liquid which contains a major proportion of methyl acrylamidoglycolate methyl ethyl and minor amounts of methyl acrylamidoglycolate butyl ether, butyl acrylamidoglycolate methyl ether and unreacted butyl acrylamidoglycolate methyl ether. Subsequent analysis indicates the major constituent to be present at about 90%.

EXAMPLE 2

Following the procedure of Example 1, 273 parts (1.34 moles) of butyl glyoxylate butyl hemiacetal is reacted with 110 parts (1.30 moles) of methacrylamide in the presence of 0.27 parts of monomethyl ether of hydroquinone. After 1.5 hours, etherification is performed in a similar manner after addition of a solution of 1.5 ml concentrated sulfuric acid in 130 ml each of butanol and butyl acetate. Subsequent methylation with a solution of 1.5 ml concentrated sulfuric acid in 425 ml methanol affords 260 parts of a bright orange colored liquid.

EXAMPLE 3

Direct Etherification and Transesterification of Butyl Acrylamidoglycolate

Aqueous glyoxylic acid (50%) in the amount of 1,980 parts (13.3 moles) and butanol in the amount of 1,210 parts (16.4 moles) are heated at 55°–60° C. and stripped under vacuum. Butanol in the amount of 1,210 parts (16.4 moles) is added and the reaction is heated at 80°–85° C. under reflux at reduced pressure for two hours. Volatiles are removed at 55°–60° C. under vacuum. Butanol in the amount of 807 parts (10.9 moles) is added and the reaction mixture is refluxed at 80°–85° C. under reduced pressure for six hours. Volatiles are again removed at 55°–60° C. under vacuum to yield 2,850 parts of butyl glyoxylate butyl hemiacetal containing about 2% butyl glyoxylate dibutyl acetal. To the crude hemiacetal (765 parts 3.0 moles) are added monomethyl ether of hydroquinone (0.65 parts and acrylamide (213 parts 3.0 moles). The reaction mixture is heated at 70°–75° C. for three hours. Three intermediate strippings under vacuum removes byproduct butanol (164 parts 2.2 moles). Methanol (870 parts, 25.5 moles) containing sulfuric acid (5.5 parts, 0.056 mole) is added. The reaction mixture is refluxed for 30 minutes and then wet methanol and butane were allowed to distill while fresh methanol (475 parts, 14.0 moles) is added in proportions approximately equal to the amount removed. The reaction mixture is then heated under reflux for an additional two hours. Treatment as described in Example 1 and neutralization of sulfuric acid catalyst with lithium oxide yielded 741 parts of orange colored liquid. Analysis of proton magnetic resonance shows the product contains approximately 90–95% methyl ether and methyl ester groups.

When a similar attempt is made to obtain methyl acrylamidoglycolate methyl ether from wet methyl glyoxylate methyl hemiacetal, a large amount of polymer formation occurs.

EXAMPLE 4

Direct Etherification and Transesterification of Isoamyl Acrylamidoglycolate

The procedure of Example 3 is followed except that isoamyl alcohol is substituted for butanol on a molar basis. Reaction of isoamyl acrylamidoglycolate with excess methanol as described therein achieves results similar to those of Example 3.

EXAMPLE 5

The procedure of Example 1 is followed except that 140 parts of propyl glyoxylate propyl hemiacetal are reacted with 57 parts of acrylamide. The intermediate propyl acrylamidoglycolate is then reacted with an additional 160 parts of propanol in the presence of 2 parts sulfuric acid. Toluene, 80 parts, present as a cosolvent to aid in water removal. Treatment of the resulting propyl acrylamidoglycolate propyl ether with 400 parts methanol as described affords 138 parts of pale yellow liquid. Analysis of the product by proton magnetic resonance shows the product contains approximately 85–90% methyl ether and methyl ester groups.

EXAMPLE 6

2-Hydroxypropyl Acrylamidoglycolate 2-Hydroxypropyl Ether

The procedure of Example 1 was followed except that the intermediate butyl acrylamidoglycolate butyl ether (55 parts) containing (0.1% by weight) methyl ether of hydroquinone was reacted with propylene glycol (40 parts) and sulfuric acid (1 part) in 450 parts butyl acetate. The reaction was run at 80°–84° C. under reduced pressure with an air bleed and the water of reaction was removed by azeotropic distillation. The material was neutralized with lithium hydroxide, the solvent distilled, and the salts filtered to give a clear yellow liquid. Analysis by $H^1$ nuclear magnetic resonance showed the major product to be 2-hydroxypropyl acrylamidoglycolate 2-hydroxypropyl ether with minor fractions of butyl acrylamidoglycolate butyl ether and the mixed ether/esters. Analysis by gel permeation chromatography showed no significant polymeric by-products.

What is claimed is:

1. A process for preparing methyl acrylamidoglycolate methyl ether in non-viscous liquid form comprising a major proportion of methyl acrylamidoglycolate methyl ether and a sufficient quantity of at least one of $C_3$ to $C_6$ alkyl acrylamido glycolate $C_3$ to $C_6$ alkyl ether, $C_3$ to $C_6$ alkyl acrylamidoglycolate methyl ether, and methyl acrylamidoglycolate $C_3$ to $C_6$ alkyl ether to provide a non-viscous liquid, which comprises reacting glyoxylic acid with a $C_3$ to $C_6$ alcohol under conditions which lead to azeotropic removal of water to provide $C_3$ to $C_6$ alkyl glyoxylate alkyl hemiacetal, reacting said $C_3$ to $C_6$ alkyl glyoxylate alkyl hemiacetal with an acrylamide while removing volatiles therefrom to provide $C_3$ to $C_6$ alkyl acrylamidoglycolate and reacting said $C_3$ to $C_6$ alkyl acrylamidoglycolate with methanol at elevated temperature in the presence of a transesterification/etherification catalyst while removing water and volatiles therefrom to provide said methyl acrylamidoglycolate methyl ether in non-viscous liquid form.

2. The process of claim 1 wherein said acrylamide is methacrylamide.

3. The process of claim 1 wherein said $C_3$ to $C_6$ alcohol is butanol.

4. The process of claim 1 wherein said transesterification/etherification catalyst is sulfuric acid.

5. A process for preparing methyl acrylamidoglycolate methyl ether in non-viscous liquid form comprising a major proportion of methyl acrylamidoglycolate methyl ether and a sufficient quantity of at least one of $C_3$ to $C_6$ alkyl acrylamidoglycolate $C_3$ to $C_6$ alkyl ether, $C_3$ to $C_6$ alkyl acrylamidoglycolate methyl ether, and methyl acrylamidoglycolate $C_3$ to $C_6$ alkyl ether to provide a non-viscous liquid, which comprises reacting glyoxylic acid with a $C_3$ to $C_6$ alcohol under conditions which lead to azeotropic removal of water to provide $C_3$ to $C_6$ alkyl hemiacetal, reacting said $C_3$ to $C_6$ alkyl alyoxylate alkyl hemiacetal with an acrylamide while removing volatiles therefrom to provide $C_3$ to $C_6$ alkyl acrylamidoglycolate, reacting said $C_3$ to $C_6$ alkyl acrylamidoglycolate with a $C_3$ to $C_6$ alcohol in the presence of an etherification catalyst under conditions which lead to the azeotropic removal of water to provide a $C_3$ to $C_6$ alkyl acrylamidoglycolate alkyl ether and then reacting said $C_3$ to $C_6$ alkyl acrylamidoglycolate alkyl ether with methanol at elevated temperature in the presence of a transesterification/transetherification catalyst while removing volatiles therefrom to provide said methyl acrylamidoglycolate methyl ether in non-viscous liquid form.

6. The process of claim 5 wherein said acrylamide is methacrylamide.

7. The process of claim 5 wherein said $C_3$ to $C_6$ alcohol is butanol.

8. The process of claim 5, wherein said etherification catalyst and said transesterification/transetherification catalyst are sulfuric acid.

* * * * *